United States Patent [19]

Gozzo et al.

[11] 4,086,226

[45] Apr. 25, 1978

[54] PROCESS FOR THE SYNTHESIS OF THIOLCARBAMATES

[75] Inventors: Franco Gozzo, Saronno (Varese); Alfredo Rondanelli; Giorgio Rossi, both of Milan, all of Italy

[73] Assignee: Montedison S.p.A., Milan, Italy

[21] Appl. No.: 763,135

[22] Filed: Jan. 27, 1977

[30] Foreign Application Priority Data

Jan. 28, 1976 Italy ................................ 19673 A/76

[51] Int. Cl.$^2$ .................. C07C 153/09; C07D 223/04
[52] U.S. Cl. .......................... 260/239 BF; 260/455 A
[58] Field of Search ...................... 260/455 A, 239 BF

[56] References Cited

U.S. PATENT DOCUMENTS

| 3,953,427 | 4/1976 | Matolesy et al. | 260/455 A |
| 3,954,729 | 5/1976 | Sato et al. | 260/455 A |

Primary Examiner—Joseph Paul Brust
Assistant Examiner—Robert C. Whittenbaugh

[57] ABSTRACT

A new and improved process for synthesizing thiolcarbamates, which are known herbicides, is disclosed. The thiolcarbamates are obtained in good yields, and without involving the use of highly poisonous, polluting, or hard-to-find reactants, by reacting dithiocarbamates with dimethylsulphoxide in the presence of a catalytic amount of iodine and at temperatures comprised between 50° and 200° C.

9 Claims, No Drawings

PROCESS FOR THE SYNTHESIS OF THIOLCARBAMATES

THE PRIOR ART

Known processes for synthesizing thiolcarbamates include the following:

(I) via carbamoylchloride

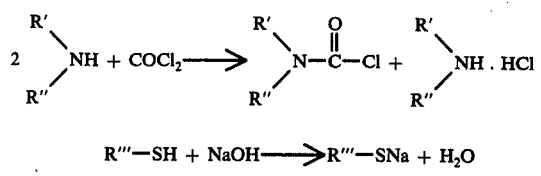

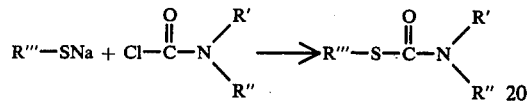

This process involves the use of phosgene, a highly toxic substance, and of R''' SH mercaptan which has an unpleasant odor and is known to be a polluting agent.

(II) via chlorothioformate

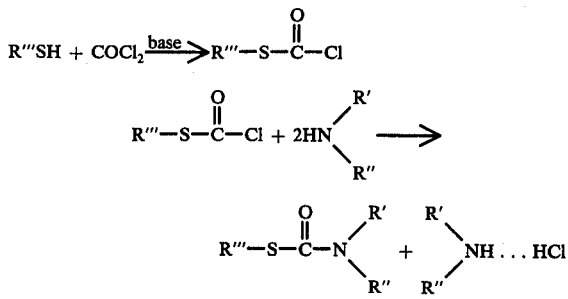

Known process (II) also requires the use of phosgene and mercaptans.

(III) via carbon oxysulphide

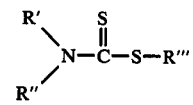

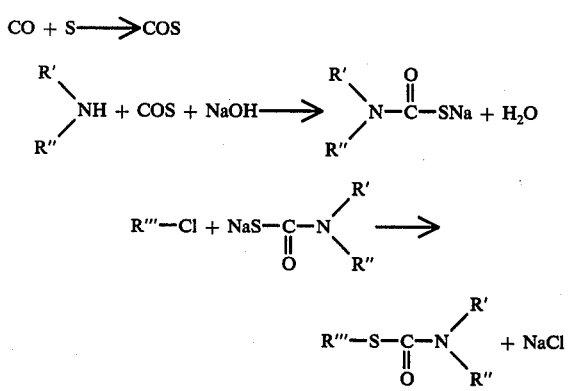

While neither phosgene nor mercaptan are used in prior art process (III), the oxysulphide is not commonly available, often difficult to procure, and, moreover, the yield obtained is not high enough for the process to be considered commercially practicable.

THE PRESENT INVENTION

An object of this invention is to provide a new and improved process for synthesizing the herbicidal thiolcarbamates in high yields and which does not have the drawbacks and disadvantages of the known processes.

This and other objects are accomplished by the present invention in accordance with which the herbicidal thiolcarbamates are synthesized in good yields from dithiocarbamates by reaction thereof with dimethylsulphoxide, in the presence of a catalytic amount of iodine, and at a temperature of from 50° to 200° C.

The starting dithiocarbamates have the general formula

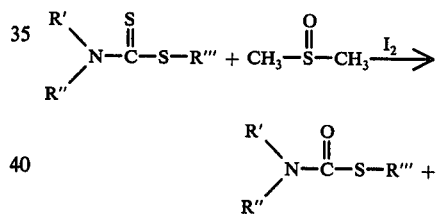

in which

R' and R", which may be the same or different, are alkyls containing from 1 to 9 carbon atoms; such alkyls substituted by halogen; or which, together, form alkylene rings incorporating nitrogen or such rings also containing heteroatoms, e.g., oxygen;

R''' is an alkyl containing 1 to 9 carbon atoms; a halogenated alkyl containing 1 to 9 carbon atoms; the phenyl radical; a substituted phenyl radical the substituents of which are selected from alkyls, oxyalkyls, or halogens; the benzl radical; or a benzyl radical substituted by alkyls, oxyalkyls, or halogens.

The reaction of the dithiocarbamates and dimethylsulphoxide, in the presence of iodine as catalyst, proceeds as follows:

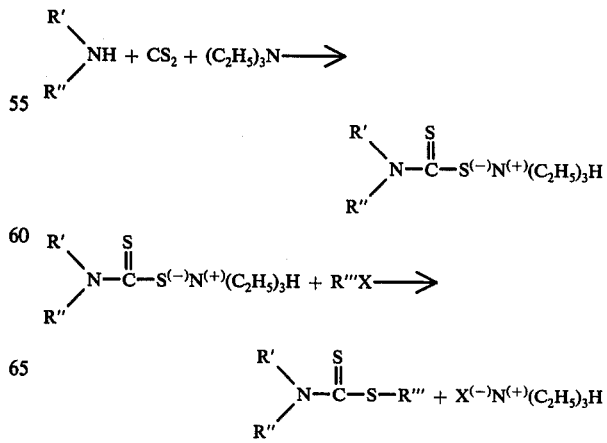

The dimethylsulphoxide may be used as a solvent for the reaction, in which case it is used in excess with respect to the necessary stoichiometric quantity.

As shown below, the preparation of the starting dithiocarbamates does not require use of either mercaptans or phosphene, or of toxic and/or polluting substances:

$$\begin{array}{c} R' \\ \diagdown \\ NH + CS_2 + (C_2H_5)_3N \longrightarrow \\ \diagup \\ R'' \end{array}$$

$$\begin{array}{c} R' \quad S \\ \diagdown \quad \| \\ N-C-S^{(-)}N^{(+)}(C_2H_5)_3H \\ \diagup \\ R'' \end{array}$$

$$\begin{array}{c} R' \quad S \\ \diagdown \quad \| \\ N-C-S^{(-)}N^{(+)}(C_2H_5)_3H + R'''X \longrightarrow \\ \diagup \\ R'' \end{array}$$

$$\begin{array}{c} R' \quad S \\ \diagdown \quad \| \\ N-C-S-R''' + X^{(-)}N^{(+)}(C_2H_5)_3H \\ \diagup \\ R'' \end{array}$$

-continued (X = Halogen).

The following examples are given to illustrate the invention in more detail and are not intended to be limiting.

EXAMPLE 1

Oxidative desulphurization of benzyl N,N-dimethyl-dithiocarbamate

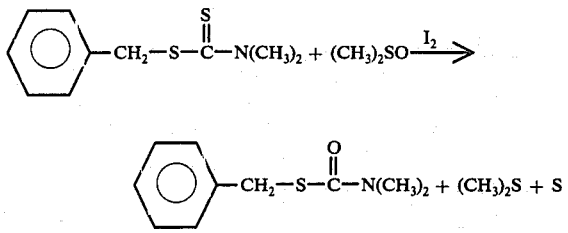

Into a 250 cc flask provided with a stirrer, a thermometer and a reflux-cooler immersed in an oil bath, there were loaded 6.5 g (equivalent to 0.03 mols) of 98% benzyl N,N-dimethyl-dithiocarbamate, 68.5 g (0.87 mols) of dimethylsulphoxide and 1.3 g (0.0005 mols) of iodine.

The bath was then slowly heated to a temperature of 120° C at which an exothermic reaction starts and the upper stratum was removed, which brought the liquid to boiling.

Gradually the temperature of the reaction mixture decreased, stabilizing at around 62° C, at which level it was maintained for 5 hours.

Thereupon, the reaction mixture was cooled down, then diluted with 50 cc of $CH_2Cl_2$, filtered on celite cake and finally the solvent was evaporated at 30° C and under a residual pressure of 15 mm Hg.

What was left was an oil which was taken up with 50 cc of $CHCl_3$, washed with 50 cc of a 10% solution of sodium thiosulphate and then with water (2 portions of 50 cc each). This chloroformic solution was then dried on $CaCl_2$ and the chloroform was evaporated at 30° C under a residual pressure of 15 mm Hg.

Thereby were obtained 5.1 g of a yellow solid having a melting point of between 36° and 41° C. The yield was 85.3%.

The elementary analysis was as follows: Theoretical S = 16.42%; actually found S = 16.56%.

The product, under liquid gas chromatography examination, proved to have a purity of 98%.

The IR spectrum was consistent with the given formula.

EXAMPLES 2–7

The conditions of Example 1 were repeated to obtain, from the corresponding thiocarbamates, thiolcarbamates of the following general formula

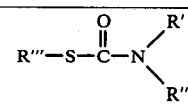

| R''' | R' | R'' | Titer(%) | Yield |
|---|---|---|---|---|
| n.C$_3$H$_7$ | CH$_2$CH(CH$_3$)CH$_3$ | CH$_2$CH(CH$_3$)CH$_3$ | 94 | 75 |
| C$_2$H$_5$ | CH$_2$CH(CH$_3$)CH$_3$ | CH$_2$CH(CH$_3$)CH$_3$ | 83 | 60 |
| C$_2$H$_5$ | n.C$_3$H$_7$ | n.C$_3$H$_7$ | 96 | 81.8 |
| n.C$_3$H$_7$ | C$_2$H$_5$ | n.C$_4$H$_9$ | 96 | 87.8 |
| C$_2$H$_5$ | (CH$_2$)$_6$ | | 97 | 80 |
| n.C$_3$H$_7$ | n.C$_3$H$_7$ | n.C$_3$H$_7$ | 94 | 91 |
| n.C$_3$H$_7$ | n.C$_3$H$_7$ | n.C$_3$H$_7$ | 94 | 81 |

What we claim is:

1. A process for preparing thiolcarbamates by desulphurization of dithiocarbamates of the formula

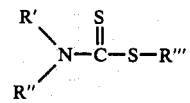

in which

R' and R'', which may be the same or different, represent alkyls containing from 1 to 9 carbon atoms; halogenated alkyls containing from 1 to 9 carbon atoms; or, together, form an alkylene ring incorporating the N atom of the thiolcarbamate; and R''' is an alkyl containing from 1 to 9 carbon atoms; halogenated alkyl containing from 1 to 9 carbon atoms; phenyl; benzyl; substituted phenyl or substituted benzyl wherein the substituents are one or more substituents selected from the group consisting of alkyl, oxy-alkyl and halogen; said process comprising reacting said thiolcarbamates with dimethylsulphoxide, in the presence of iodine as catalyst and at a temperature of from 50° to 200° C, according to the following reaction:

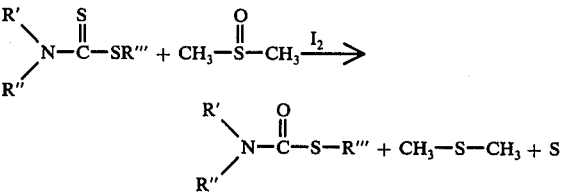

and recovering the thiolcarbamate formed from the reaction mixture.

2. The process of claim 1, in which the dimethylsulphoxide is the solvent for the reaction and is used in an amount in excess of the stoichiometric amount.

3. The process of claim 1, in which the dithiocarbamate reacted with dimethylsulphoxide in the presence of iodine as catalyst is benzyl N,N-dimethyl-dithiocarbamate.

4. The process of claim 1, in which the dithiocarbamate reacted with dimethylsulphoxide in the presence of iodine as catalyst is propyl N,N-dimethyl-dithiocarbamate.

5. The process of claim 1, in which the dithiocarbamate reacted with dimethylsulphoxide in the presence of iodine as catalyst is ethyl N,N-dimethyl-dithiocarbamate.

6. The process of claim 1, in which the dithiocarbamate reacted with the dimethylsulphoxide is ethyl-N,N-di-n-propyl-dithiocarbamate.

7. The process of claim 1, in which the dithiocarbamate reacted with the dimethylsulphoxide is n-propyl-N,N-ethyl-n-butyl-dithiocarbamate.

8. The process of claim 1, in which the dithiocarbamate reacted with the dimethylsulphoxide is ethyl-N,N-hexamethylene-dithiocarbamate.

9. The process of claim 1, in which the dithiocarbamate reacted with the dimethylsulphoxide is n-butyl-N,N-n-butyl-dithiocarbamate.

* * * * *